United States Patent
Yonce

(10) Patent No.: US 7,336,998 B2
(45) Date of Patent: Feb. 26, 2008

(54) EXTERNAL DISCRIMINATION BETWEEN PACE PULSES AT DIFFERENT HEART LOCATIONS

(75) Inventor: David J. Yonce, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 569 days.

(21) Appl. No.: 10/608,825

(22) Filed: Jun. 24, 2003

(65) Prior Publication Data

US 2004/0267146 A1 Dec. 30, 2004

(51) Int. Cl.
*A61N 1/08* (2006.01)
*A61B 5/04* (2006.01)

(52) U.S. Cl. .......................... 607/27; 600/509
(58) Field of Classification Search ............. 607/51, 607/9, 27; 600/509
See application file for complete search history.

(56) References Cited

U.S. PATENT DOCUMENTS

| | | | |
|---|---|---|---|
| 3,742,938 A | 7/1973 | Stern | 128/2.05 |
| 4,539,999 A | 9/1985 | Mans | 128/696 |
| 4,664,116 A | 5/1987 | Shaya et al. | 128/419 |
| 4,796,638 A | 1/1989 | Sasaki | 128/696 |
| 4,838,278 A * | 6/1989 | Wang et al. | 600/510 |
| 4,926,868 A * | 5/1990 | Larsen | 600/407 |
| 5,078,133 A * | 1/1992 | Heinz et al. | 607/17 |
| 5,127,401 A * | 7/1992 | Grevious et al. | 607/27 |
| 5,231,990 A * | 8/1993 | Gauglitz | 600/510 |
| 5,331,966 A * | 7/1994 | Bennett et al. | 600/508 |
| 5,425,373 A * | 6/1995 | Causey, III | 600/510 |
| 5,448,997 A | 9/1995 | Kruse et al. | 128/697 |
| 5,522,851 A | 6/1996 | Fayram | |
| 5,527,346 A | 6/1996 | Kroll | |
| 5,545,202 A * | 8/1996 | Dahl et al. | 607/129 |
| 5,554,178 A | 9/1996 | Dahl et al. | |
| 5,658,319 A | 8/1997 | Kroll | |

(Continued)

FOREIGN PATENT DOCUMENTS

WO   WO-00/19470   4/2000

OTHER PUBLICATIONS

Johnson, Richard, and Mark H. Swartz. A Simplified Approach to Electrocardiography. Philadelphia: W.B. Saunders Company, 1986. 13-16, 23-25.*

(Continued)

*Primary Examiner*—Angela D. Sykes
*Assistant Examiner*—Christopher A. Flory
(74) *Attorney, Agent, or Firm*—Schwegman, Lundberg, & Woessner, P.A.

(57) ABSTRACT

This document discusses, among other things, an external device capable of independently distinguishing between pace pulses delivered by an implantable cardiac rhythm management device to different locations of a subject's heart. In one example, polarity of the pace pulses is detected along two different electrocardiograph (ECG) vectors defined by three external skin electrodes. In a further example, the detection of a ventricular depolarization is also used to assign location information to pace pulses. In another example, characterizing information (e.g., polarity, amplitude, pulsewidth, time difference between a pace pulse and a corresponding heart depolarization) is used to classify pace pulses into distinct classes to which location information can be assigned. An ECG display/recorder of the external device is capable of annotating pace pulses or markers using the location information.

21 Claims, 8 Drawing Sheets

U.S. PATENT DOCUMENTS

| | | | |
|---|---|---|---|
| 5,701,907 A * | 12/1997 | Klammer | 600/509 |
| 5,725,559 A * | 3/1998 | Alt et al. | 607/5 |
| 5,738,104 A | 4/1998 | Lo et al. | 128/706 |
| 5,908,151 A | 6/1999 | Elias | |
| 5,913,828 A * | 6/1999 | Russell | 600/509 |
| 6,006,133 A | 12/1999 | Lessar et al. | |
| 6,009,348 A | 12/1999 | Rorvick et al. | |
| 6,064,906 A * | 5/2000 | Langberg et al. | 600/518 |
| 6,477,404 B1 | 11/2002 | Yonce et al. | |
| 6,496,715 B1 * | 12/2002 | Lee et al. | 600/424 |
| 6,505,067 B1 * | 1/2003 | Lee et al. | 600/509 |
| 6,760,622 B2 * | 7/2004 | Helland et al. | 607/9 |
| 6,766,190 B2 * | 7/2004 | Ferek-Petric | 600/512 |
| 2001/0034487 A1 * | 10/2001 | Cao et al. | 600/508 |
| 2003/0083716 A1 * | 5/2003 | Nicolelis et al. | 607/45 |
| 2004/0019288 A1 * | 1/2004 | Kinast | 600/509 |

OTHER PUBLICATIONS

"U.S. Appl. No. 06-20-2002 Non Final office action mailed Jan. 29, 2002", 10 pgs.

"U.S. Appl. No. 06-20-2002 Notice of allowance mailed Jun. 20, 2002", 5 pgs.

"U.S. Appl. No. 06-20-2002 Response filed Apr. 29, 2002 to Non Final office action mailed Jan. 29, 2002", 4 pgs.

"U.S. Appl. No. 10/251,310 Amendment Under 37 CFR 1.312 filed May 13, 2004", 10 pgs.

"U.S. Appl. No. 10/251, 310 Notice of allowance mailed Feb. 13, 2004", 10 pgs.

* cited by examiner

EXTERNAL DISCRIMINATION BETWEEN PACE PULSES AT DIFFERENT HEART LOCATIONS

CROSS REFERENCE TO RELATED APPLICATIONS

This patent application is related to U.S. patent application Ser. No. 09/516,533, filed on Mar. 1, 2000, now issued as U.S. Pat. No. 6,477,404, entitled SYSTEM AND METHOD FOR DETECTION OF PACING PULSES WITHIN ECG SIGNALS, which is assigned to Cardiac Pacemakers, Inc., and which is incorporated herein by reference in its entirety.

TECHNICAL FIELD

This document relates generally to systems, devices, and methods using external electrocardiograph (ECG) signals and particularly, but not by way of limitation, to external discrimination between pace pulses

BACKGROUND

Implantable medical devices include, among other things, cardiac rhythm management (CRM) devices such as pacers, cardioverters, defibrillators, cardiac resynchronization therapy (CRT) devices, as well as combination devices that provide more than one of these therapy modalities to a subject. External electrocardiograph (ECG) devices include, among other things, programmers (for programming implantable medical devices), recorders, monitors, or any other device capable of acquiring external ECG signals, such as by using external surface ECG electrodes attached to a patient's skin. Such externally acquired ECG signals typically include information about pacing pulses being delivered to the patient to evoke heart contractions. However, external ECG devices typically cannot independently distinguish between pacing pulses being delivered at different heart locations.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 2 is a schematic diagram illustrating generally one example of an external device, such as a remote programmer for an implantable device, an ECG monitor, and/or an ECG recorder, or the like.

DETAILED DESCRIPTION

In the following detailed description, reference is made to the accompanying drawings which form a part hereof, and in which is shown by way of illustration specific embodiments in which the invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

Figure 1:
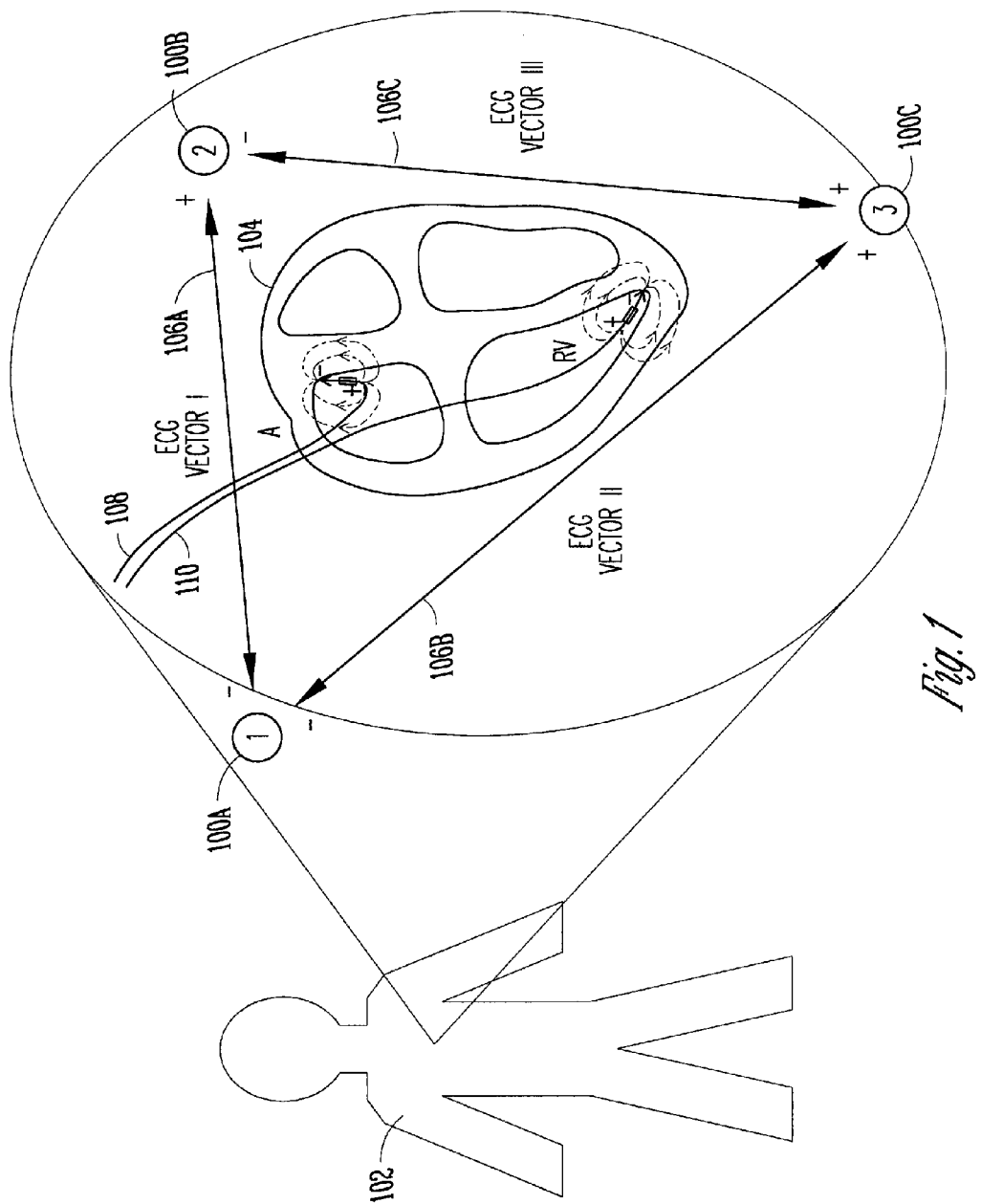
FIG. 1 is a schematic diagram illustrating generally one example of a configuration of electrodes associated with a human or other subject to receive signals, such as heart signals from the subject's heart.

FIG. 1 is a schematic diagram illustrating generally, by way of example, but not by way of limitation, one example of a configuration of electrodes 100A-C associated with a human or other subject 102 to receive signals, such as heart signals from the subject's heart 104. FIG. 1 illustrates external electrodes 100A-C, such as surface ECG electrodes externally attached to the subject's skin. In the relative arrangement illustrated in the example of FIG. 1, a first electrode 100A is attached on or near the subject's right arm, a second electrode 100B is attached on or near the subject's left arm, and a third electrode 100C is attached below the heart 104, such as on the subject's thorax or on one of the subject's legs.

In the example of FIG. 1, the first electrode 100A is negative with respect to the second electrode 100B and the third electrode 100C. The second electrode 100B is positive with respect to the first electrode 100A and negative with respect to the third electrode 100C. The third electrode 100C is positive with respect to the first electrode 100A and the second electrode 100B. The electrodes 100A-C define ECG vectors 106A-C.

FIG. 1 also illustrates a J-shaped atrial bipolar intravascular pacing lead 108. The lead 108, which is located in a right atrium chamber of the heart 104, includes a distal tip electrode and a slightly more proximal ring electrode. FIG. 1 includes electric field lines illustrating an electric field created by delivery of an atrial pace pulse between these ring and tip electrodes, using the tip electrode as a cathode and the ring electrode as an anode.

FIG. 1 also illustrates a ventricular bipolar intravascular pacing lead 110. The lead 110 includes a distal tip electrode (near an apex of the right ventricle) and a slightly more proximal ring electrode. Electric field lines illustrate an electric field created by delivery of a ventricular pace pulse between these ring and tip electrodes, using the tip electrode as a cathode and the ring electrode as an anode.

Figure 2:
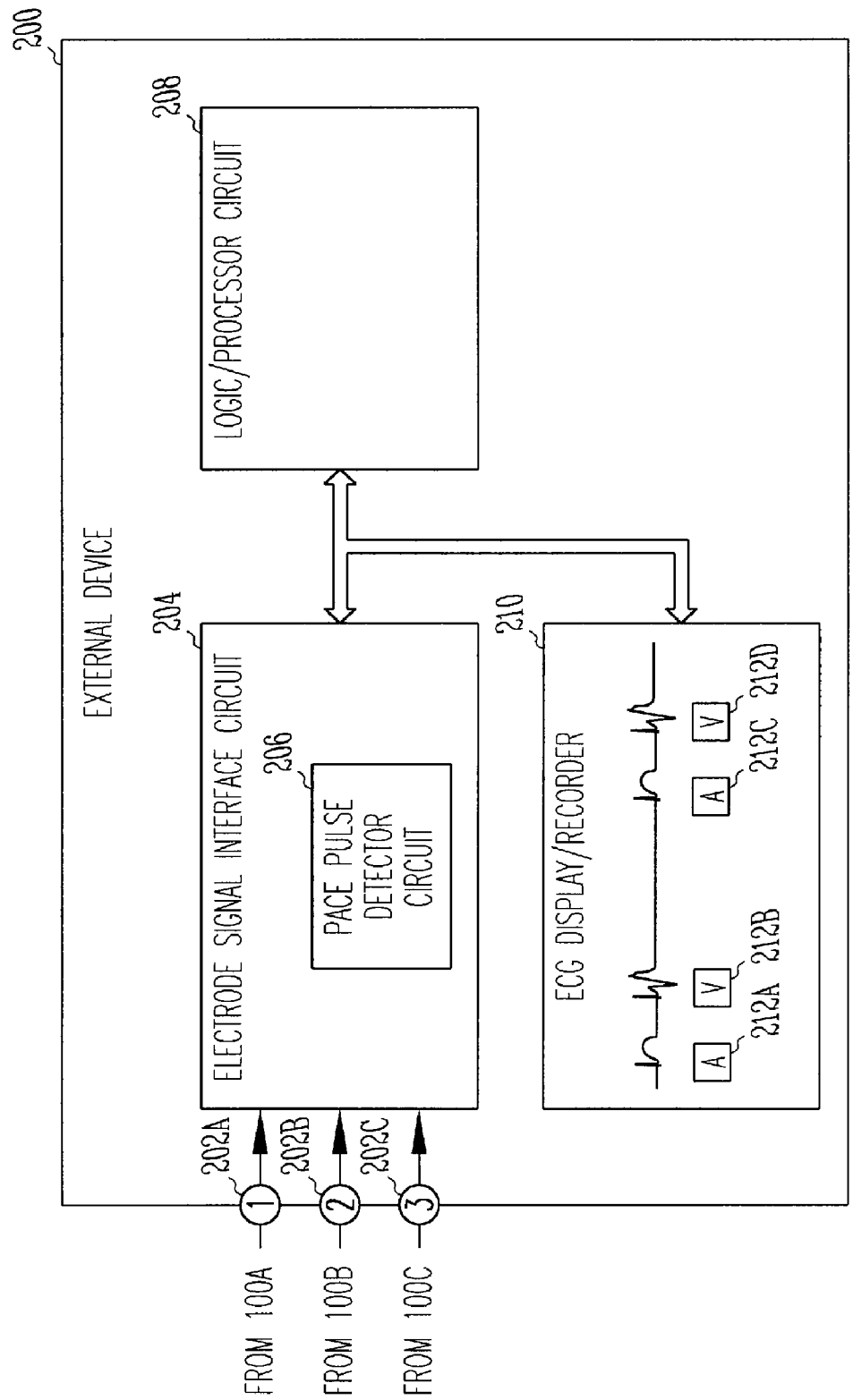

FIG. 2 is a schematic diagram illustrating generally, by way of example, but not by way of limitation, one example of an external device 200, such as a remote programmer for an implantable device, an ECG monitor, and/or an ECG recorder, or the like. The external device 200 includes a first input terminal 202A, a second input terminal 202B, and a third input terminal 202C, which are respectively coupled to the first electrode 100A, the second electrode 100B, and the third electrode 100C. An electrode signal interface circuit 204 is coupled to the input terminals 202A-C to receive heart signals from the electrodes 100A-C. In this example, the electrode signal interface circuit 204 includes at least one pace pulse detector circuit 206. One example of a pace pulse detector circuit 206 is described in Yonce et al. U.S. Pat. No. 6,477,404 entitled SYSTEM AND METHOD FOR DETECTION OF PACING PULSES WITHIN ECG SIGNALS, which is assigned to Cardiac Pacemakers, Inc., and which is incorporated herein by reference in its entirety, including its description of a pace pulse detector circuit.

The pace pulse detector circuit 206 recognizes at least two distinct pace pulses, such as the bipolar atrial and ventricular pace pulses delivered by the arrangement of lead electrodes illustrated in FIG. 1. In one example, the pace pulse detector circuit 206 provides an output indicating the polarity of each detected pace pulse. A logic circuit 208 receives information about the pace pulses, such as the polarity information referred to above. The logic circuit 208 can be implemented in many different forms, such as a digital logic circuit, or as a sequence of instructions executed on a microprocessor, controller, or other processor circuit, or using any other desired combination of hardware, firmware, and/or software. In this example, the logic circuit 208 uses the polarity information to classify the pace pulses as atrial or ventricular, as discussed below. The device 200 also includes an ECG display/recorder 210, for displaying and/or recording an ECG signal obtained from the subject. In one example, such as illustrated in FIG. 2, the display includes annotations 212 as to whether a particular pace pulse was classified as atrial or ventricular.

Figure 3:
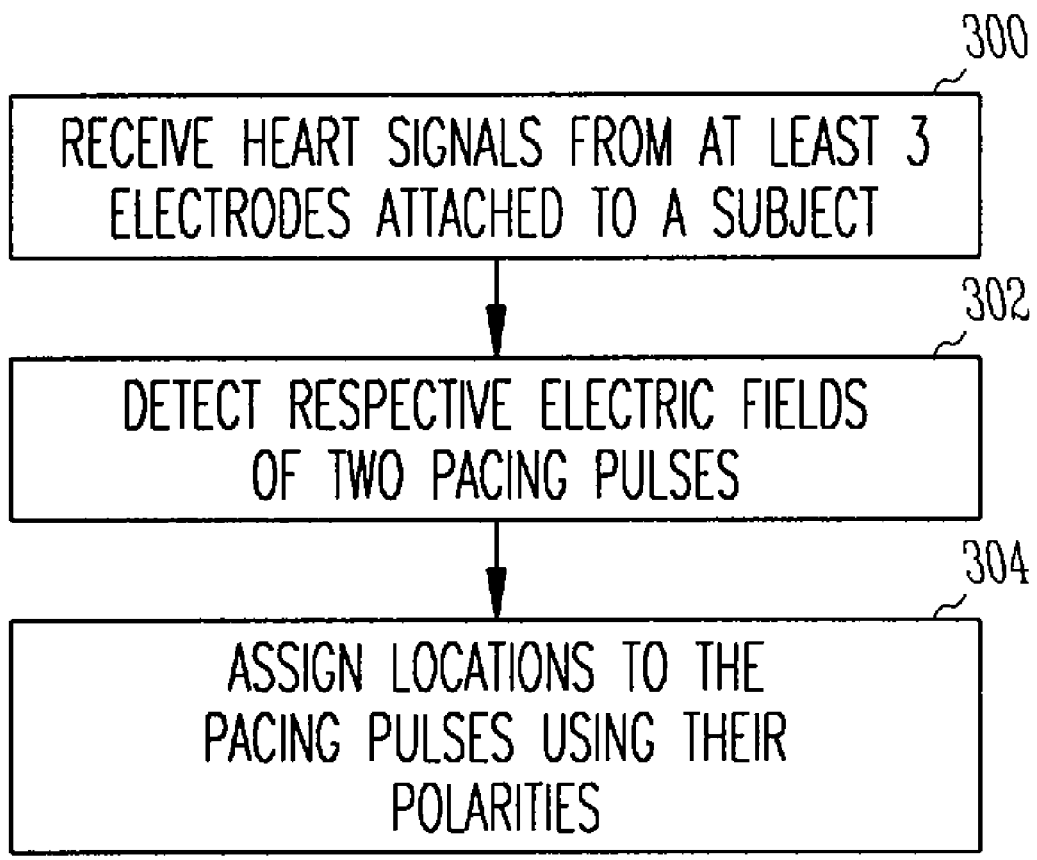
FIG. 3 is a flow chart illustrating generally one method of using the devices illustrated in FIGS. 1-2.

FIG. 3 is a flow chart illustrating generally one method of using the devices illustrated in FIGS. 1-2. At 300, heart signals are received from at least three electrodes attached to the subject 102, such as by using the electrodes 100A-C. At 302, electric fields associated with two distinct pacing pulses are detected. For the lead configuration illustrated in FIG. 1, the third electrode 100C is positive with respect to each of the first electrode 100A and the second electrode 100B. Therefore, an atrial pacing pulse will be detected with a positive polarity along both the second ECG vector 106B and the third ECG vector 106C, as illustrated by the electric field lines associated with the atrial electrodes in FIG. 1. Similarly, a ventricular pacing pulse will be detected with a negative polarity along both the second ECG vector 106B and the third ECG vector 106C, as illustrated by the electric field lines associated with the ventricular electrodes in FIG. 1. Of course, other lead configurations (e.g., having differently oriented bipolar electrodes) could lead to different results, but the same principles discussed in this document would still be applicable.

Continuing with respect to the lead configuration illustrated in FIG. 1, at 304 of FIG. 3, locations are assigned to the detected pace pulses using this polarity information. If a pace pulse was detected as positive in polarity along both the second ECG vector 106B and the third ECG vector 106C, then that pace pulse is assigned an atrial location. If a pace pulse was detected as negative in polarity along both the second ECG vector 106B and the third ECG vector 106C, then that pace pulse is assigned a ventricular location. One example of these location discrimination assignments, for two different pace pulses, is illustrated in Table 1. In a further example, these location assignments are used to provide annotations 212 (e.g., "A" for atrial, and "V" for ventricular) to markers indicative of the pace pulses displayed on the ECG display/recorder 210.

TABLE 1

Discrimination criteria when one pace has the same polarity on two ECG vectors.

| Pace 1 Polarity | | Pace 2 Polarity | | Location Discrimination Assignments | |
| --- | --- | --- | --- | --- | --- |
| Vector II (106B) | Vector III (106C) | Vector II (106B) | Vector III (106C) | Pace 1 | Pace 2 |
| + | + | + | − | A | V |
|   |   | − | + |   |   |
|   |   | − | − |   |   |
| − | − | + | − | V | A |
|   |   | − | + |   |   |
|   |   | − | − |   |   |

Figure 4:
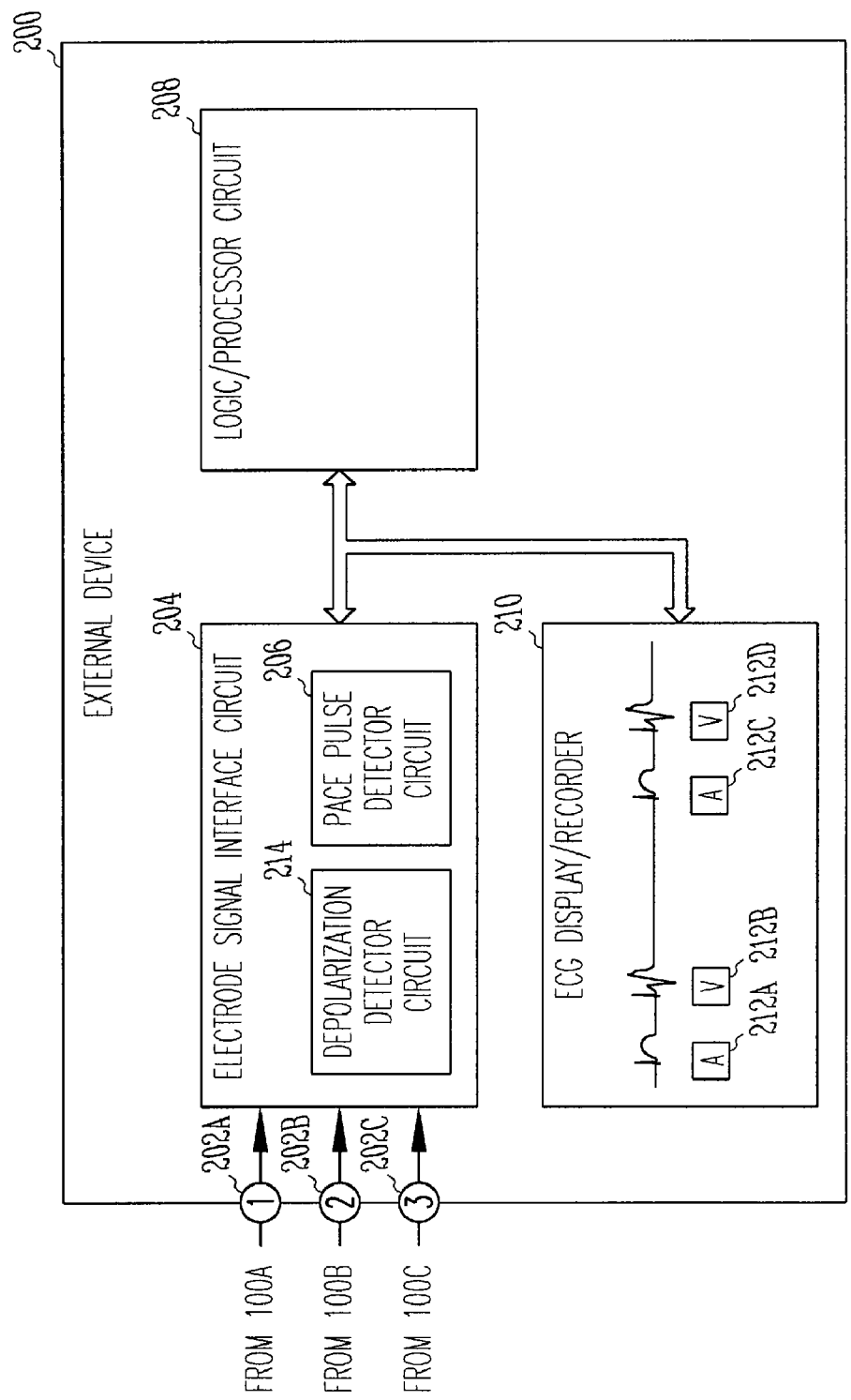
FIG. 4 is a schematic diagram, similar to FIG. 2, but including a depolarization detector circuit to assist in providing location assignments.

FIG. 4 is a schematic diagram, similar to FIG. 2, but including a depolarization detector circuit 214 to assist in providing location assignments, such as when a pace pulse is detected as having different polarities on the second ECG vector 106B and the third ECG vector 106C. In this example, the depolarization detector circuit 214 includes a level detector circuit (or other suitable circuit, which may include filtering over a particular band and/or other signal processing) capable of distinguishing smaller amplitude atrial heart depolarizations from larger amplitude ventricular heart depolarizations.

Figure 5:
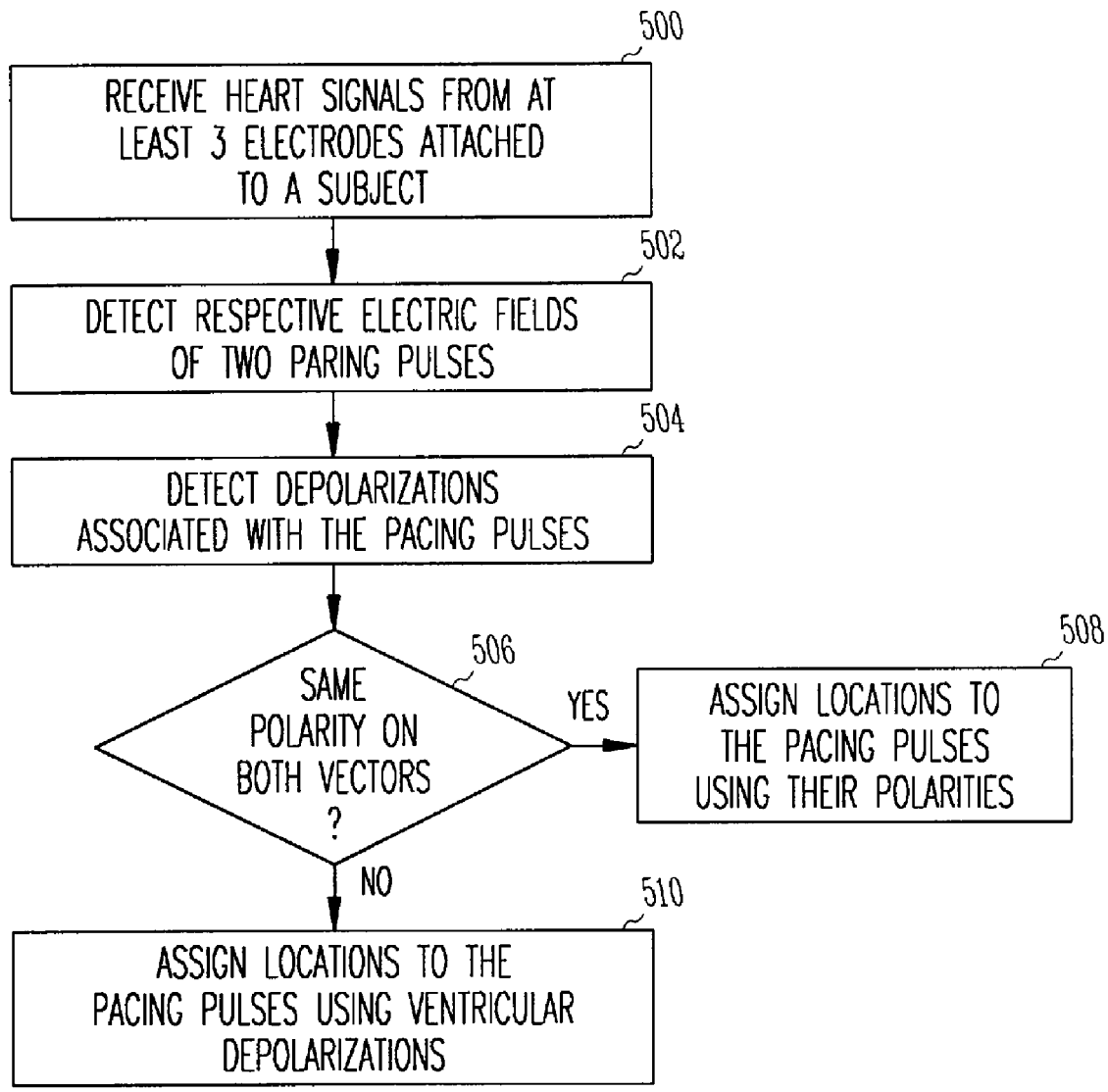
FIG. 5 is a flow chart of a method for assigning locations to pace pulses, such as by using polarity information and depolarization information.

FIG. 5 is a flow chart of a method for assigning locations to pace pulses, such as by using polarity information and depolarization information. At 500, heart signals are received, such as described above with respect to 300. At 502, respective electric fields of two pacing pulses are detected, such as described above with respect to 302. At 504, depolarizations associated with the pace pulses (if any) are detected. In one example, a detected depolarization is associated with a particular pace pulse if it occurs within a predetermined or designated time interval of the pace pulse. In another example, the detected depolarization is associated with a particular pace pulse if it occurs within a predetermined or designated time interval after the pace pulse. Moreover, ventricular depolarizations can be distinguished from atrial depolarizations, as discussed above, such as by using a level detector circuit, a morphology detector circuit, or any other one of several known techniques for distinguishing between atrial and ventricular heart depolarizations. At 506, if a pace pulse is observed with the same polarity on both the second vector 106B and the third vector 106C, then locations are assigned to the pace pulse using the polarity information at 508, such as discussed above with respect to 304. Otherwise, at 510, locations are assigned to the pacing pulses using detected ventricular depolarizations. For example, if a pacing pulse is followed by a detected ventricular depolarization within a predetermined time period (e.g., between 15 milliseconds and 200 milliseconds, such as 100 milliseconds), then that pace pulse is deemed a ventricular pace pulse. Otherwise it is deemed an atrial pace pulse. In an alternative example, such as where the atrioventricular (AV) delay of the implanted device is known, then the AV delay is used as a maximum limit on this predetermined time period for detecting a ventricular depolarization to distinguish a ventricular pace pulse from an atrial pace pulse.

One example of these location discrimination assignments, for two successive pace pulses (where each pace pulse is observed with different polarities on the second vector 106B and the third vector 106C) is illustrated in Table 2.

TABLE 2

Discrimination criteria using ventricular depolarization (e.g., R-wave) detection

| Pace 1 Polarity | | | Pace 2 Polarity | | | Location Discrimination Assignments | |
|---|---|---|---|---|---|---|---|
| Vector II (106B) | Vector III (106C) | R-wave after pace? | Vector II (106B) | Vector III (106C) | R-wave after pace? | Pace 1 | Pace 2 |
| + | − | Yes | − | + | No | V | A |
| + | − | No | − | + | Yes | A | V |
| + | − | Yes | − | + | Yes | Indeterminate | |
| + | − | No | − | + | No | Indeterminate | |

Figure 6:
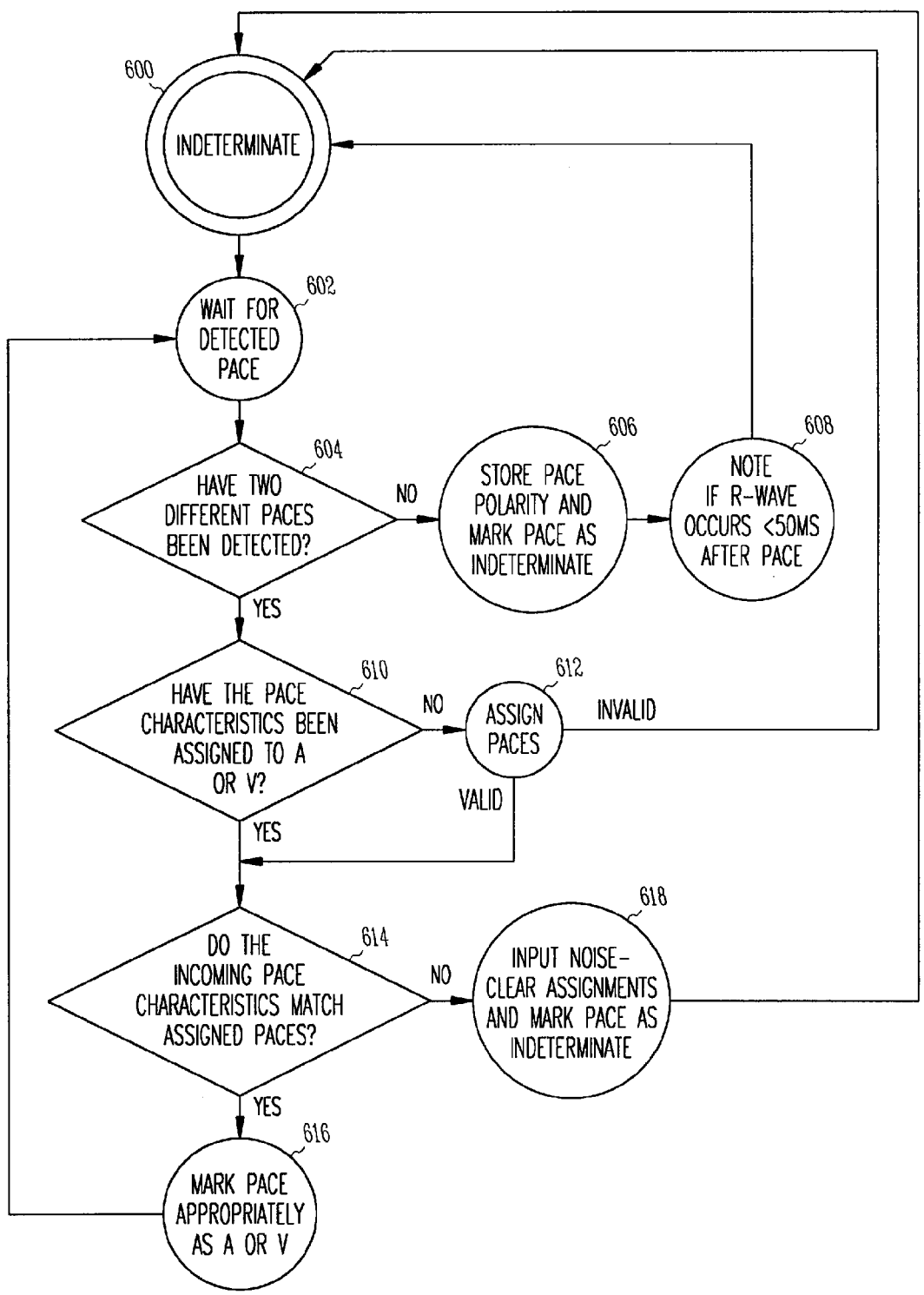
FIG. 6 is a flow chart illustrating generally an example of a method for discriminating between pace pulses.

FIG. 6 is a flow chart illustrating generally, by way of example, but not by way of limitation, an example of a method for discriminating between pace pulses. At 600, the method is initiated in an "indeterminate" state with respect to any pace pulse locations. At 602, the method includes waiting for a detected pace pulse. At 604, a determination is made (e.g., using polarity) of whether two different pace pulses have been detected. If one of the detected pace pulses displays a different polarity characteristic—on at least one of the vectors 106—from the other detected pace pulse, then these two detected pace pulses are deemed different. If the two pace pulses are not different at 604, then, at 606, the pace polarity is stored and the detected pace is deemed indeterminate. If the pace pulse (or a marker indicative of a pace pulse) is being displayed on an ECG monitor, then that pulse or marker is either not labeled with location annotations, or is labeled as indeterminate. Then, at 608, it is noted whether a ventricular depolarization (e.g., an R-wave) occurs within a predetermined time period of the pace (e.g., within 50 milliseconds after the pace), before process flow returns to the indeterminate state at 600.

At 604, if two different pace pulses have been detected, then, at 610, it is determined whether the most recently detected pace has been assigned to an atrial location or to a ventricular location, such as by using the polarity discrimination techniques discussed above. If no such location has been assigned, then, at 612, the pace is assigned to either an atrial location or to a ventricular location, such as by using the polarity technique discussed above. If the polarity technique yields an indeterminate location assignment (e.g., such as illustrated in Table 2) then process flow returns to the indeterminate state at 600. Otherwise if, at 614, using the polarity-based location assignment technique discussed above, the most recently detected pace pulse can be classified consistently with the location assignments for previous paces, then, at 616, a display of the pace pulse (or a marker indicative of the pace pulse) is provided with annotation 212 indicating the atrial or ventricular location of the pace pulse, and process flow returns to 602 to wait for another detected pace. Otherwise, at 618, input "noise" is deemed to exist, the previous location assignments are cleared, and the incoming pace is marked as indeterminate, and process flow returns to the indeterminate state at 600.

The lead configuration illustrated in FIG. 1 used bipolar pacing leads, that is, a lead with electrodes that are relatively close to each other (e.g., ring and tip), for delivering a pace pulse therebetween. However, cardiac rhythm management systems are also typically capable of pacing in a "unipolar" mode. More particularly, the intravascular leads are typically connected to a pectorally or abdominally implanted cardiac rhythm management device including a housing. This housing may include a housing electrode. In unipolar mode, pace pulses are typically delivered using this housing electrode as an anode and a cathode located in or near the heart, such as one of the ring or tip electrodes illustrated in FIG. 1. This typically produces large negative pacing pulses detected on the second ECG vector 106B and the third ECG vector 106C—regardless of whether the electrodes located within the heart 104 are located in an atrium or a ventricle. Therefore, in unipolar pacing mode, polarity information alone is typically insufficient to discriminate between atrial and ventricular pace pulses.

Moreover, certain other pacing therapies, such as to treat congestive heart failure (CHF), may include a lead placed in association with a left ventricle, such as to resynchronize or coordinate left and right ventricular contractions. Instead of using the intracardiac lead placement of FIG. 1, which positions the leads 108 and 110 in a right atrium and a right ventricle, respectively, left ventricular leads are typically not introduced directly into the left ventricle heart chamber. Instead, the left ventricular lead is typically introduced within a blood vessel (e.g., the coronary sinus and/or great cardiac vein) that is very close to the left ventricle. Because the cardiac vasculature can vary from patient to patient, the polarity of bipolar left ventricular pacing pulses (e.g., detected on the second ECG vector 106B and the third ECG vector 106C) can be difficult to predict. Moreover, adding a third (e.g., left ventricular) pacing electrode to first and second (e.g., right atrial and right ventricular) pacing electrodes will increase the difficulty of distinguishing between pacing pulses delivered to these different locations (e.g., right atrium, right ventricle, and left ventricle).

To accommodate unipolar pacing and/or bi-ventricular pacing—or various other more complicated pacing modalities—the external device 200 of FIG. 2 includes a pacing pulse detector circuit 206 that is capable of providing one or more other characteristics of pace pulses that are capable of distinguishing between pace pulses delivered to different locations. For example, by sampling the ECG data obtained from the electrodes 100A-C at a sampling rate of at least 60 kHz, an amplitude and/or a pulsewidth of pace pulses can be measured by the pacing pulse detector circuit 206. Moreover, polarity information may also be obtained, such as discussed above. Furthermore, the pace pulse detector circuit 206 can be used in combination with the depolarization detector circuit 214 to provide further characterizing information—such as a time difference between a pace pulse and a depolarization occurring soon (e.g., within a predetermined time period) before and/or after the pace pulse. The characterizing information (e.g., polarity, amplitude, pulsewidth, time difference with respect to a heart depolarization, etc.) can be used to recognize and distinguish between different classes of paces.

Figure 7:
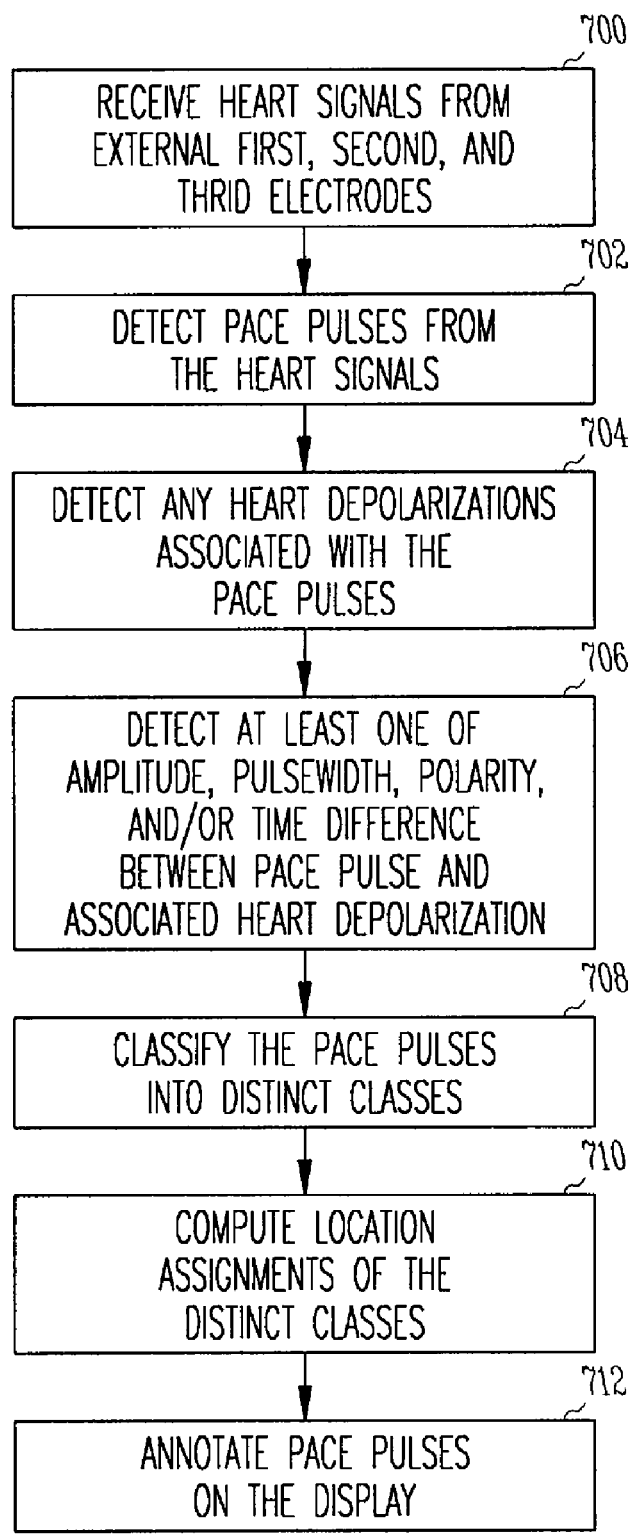
FIG. 7 is a flow chart illustrating generally one method of classifying pace pulses into distinct classes using characterizing information, and then computing location assignments for the distinct classes.

FIG. 7 is a flow chart illustrating generally, by way of example, but not by way of limitation, one method of classifying pace pulses into distinct classes using characterizing information, and then computing location assignments for the distinct classes. At 700, heart signals are received, such as from external electrodes 100A-C of FIG. 1, as described above. At 702, pace pulses are detected from the heart signals, such as by using the pace pulse detector circuit 206, as described above. At 704, any heart depolarizations associated with the pace pulses are detected, such as by using the depolarization detector circuit 214 as described above. In one example, a detected depolarization is deemed to be associated with a particular pace pulse if it occurs within a predetermined time interval of the pace pulse. In another example, the detected depolarization is deemed to be associated with a particular pace pulse if it occurs within a predetermined time interval after the pace pulse. Moreover, ventricular depolarizations can be distinguished from atrial depolarizations, as discussed above, such as by using a level detector circuit, a morphology detector circuit, or any other one of several known techniques for distinguishing between atrial and ventricular heart depolarizations.

At 706, characterizing information is obtained. As discussed above, this may include detecting at least one of a pace pulse amplitude, a pulsewidth of a pace pulse, and/or a polarity of a pace pulse. It may also include measuring a time difference between a pace pulse and an associated (earlier or later) depolarization. Information about the type of depolarization (e.g., atrial or ventricular) is available, as discussed above, such as by using a level detector circuit, a morphology detector circuit, etc.

At 708, the pace pulses are classified into distinct classes using the characterizing information. For example, a cardiac rhythm management device may be programmed to output an atrial pulse amplitude of 2.0 Volts, and a ventricular pulse amplitude of 3.5 Volts. By recognizing that 2.0 Volt pace pulses are different than 3.5 Volt pace pulses, different classes of pace pulses are therefore obtained. Similarly, cardiac rhythm management device may be programmed to output a right ventricular pace pulse having a pulsewidth of 0.5 milliseconds and a left ventricular pace pulse having a pulsewidth of 0.7 milliseconds. By recognizing that 0.5 millisecond pulses are different from 0.7 millisecond pulses, different classes of pace pulses are therefore obtained. In another example, for a CHF patient with a cardiac rhythm management device delivering pacing pulses to both right and left ventricles to coordinate their respective contractions, a time difference between a right ventricular pacing pulse and its associated ventricular depolarization may be different from a time difference between a left ventricular pacing pulse and its associated ventricular depolarization. Moreover, the time differences between right and left ventricular pacing pulses and their associated ventricular depolarization will be different from the time difference between an atrial pacing pulse and the ventricular depolarization associated with the left and right ventricular pacing pulses. These time differences can be used to distinguish between the right and left ventricular pace pulses. (However, it may not necessarily allow determination of which pace originated in the right ventricle and which pace originated in the left ventricle). Similarly, these time differences can be used to distinguish between the right and left ventricular pace pulses and an atrial pace pulse. Therefore, the time differences permit the right and left ventricular pace pulses and the atrial pace pulse to be classified into separate and distinct classes at 708. At 710, location assignments (e.g., V1, V2, and A) of the distinct classes are computed, At 712, pace pulses are annotated on the display using the computed location assignments.

For bi-ventricular pacing, one example of computing the location assignments at 710 is described in Table 3.

TABLE 3

Discrimination criteria for multi-site (e.g., biventricular) pacing

| R-wave within 100 ms? | | | Pacing Pulse Assignments | | |
|---|---|---|---|---|---|
| Pace 1 | Pace 2 | Pace 3 | Pace 1 | Pace 2 | Pace 3 |
| No | No | No | | Invalid | |
| No | No | Yes | | Invalid | |
| No | Yes | No | | Invalid | |
| No | Yes | Yes | A | V1 | V2 |
| Yes | No | No | | Invalid | |
| Yes | No | Yes | V1 | A | V2 |
| Yes | Yes | No | V1 | V2 | A |
| Yes | Yes | Yes | | Invalid | |

In Table 3, detection of a ventricular depolarization (e.g., an R-wave) within a predetermined time period (e.g., 100 milliseconds) either before or after a pace pulse of a particular class is delivered, identifies pace pulses of that class as being associated with a ventricle. For such ventricular pace pulses, the characterizing information distinguishes the pace pulses as being delivered at two different ventricular locations (e.g., V1, V2): In one example, the pace pulses, or corresponding markers, are annotated with corresponding identifiers. In another example, the display provides other useful information such as, for example, the number of distinct classes of pacing pulses that were detected (e.g., "three different classes of pacing pulses were detected").

Figure 8:
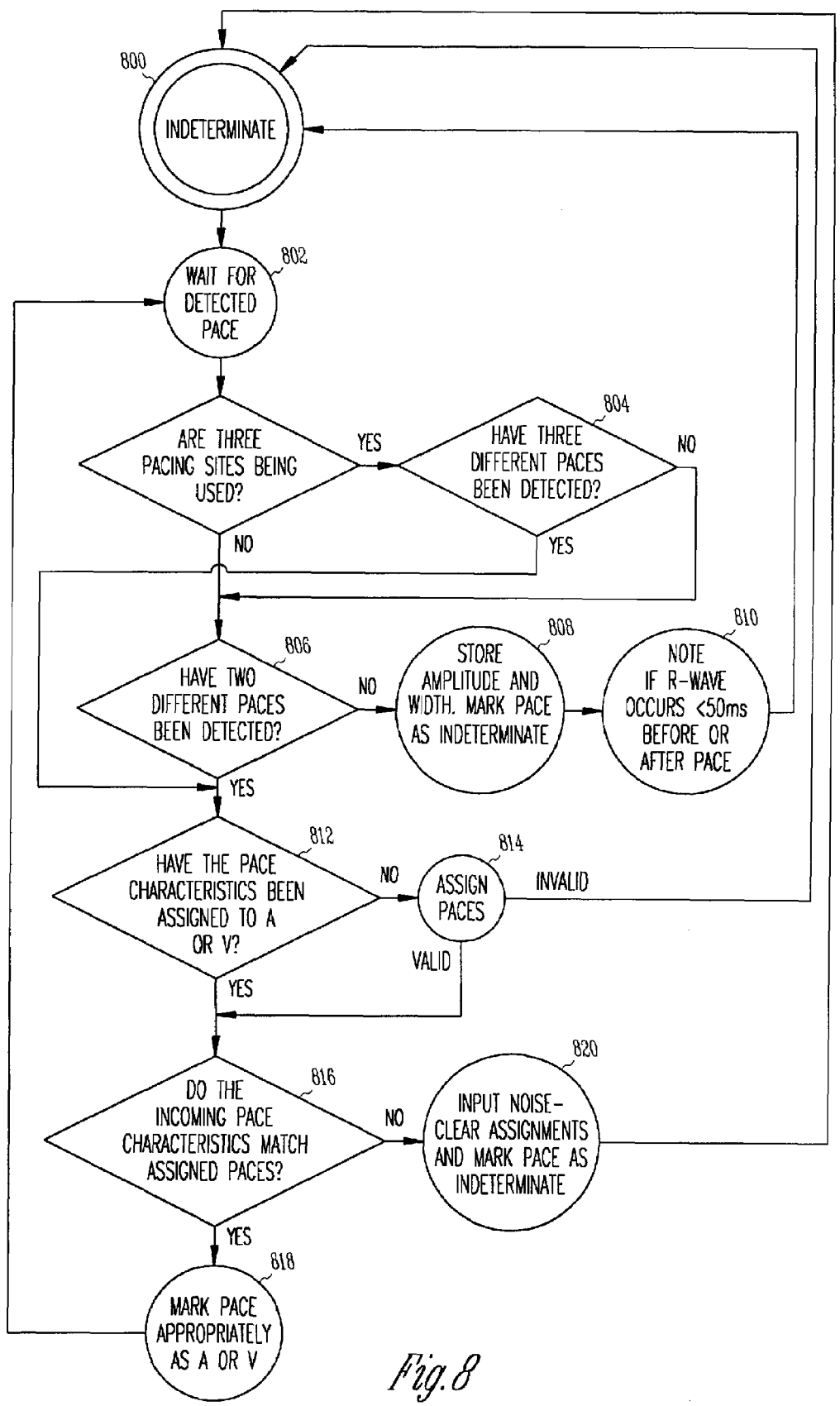
FIG. 8 is a flow chart illustrating generally, by way of example, but not by way of limitation, one method of discriminating between pace pulses—including for biventricular pacing.

FIG. 8 is a flow chart illustrating generally, by way of example, but not by way of limitation, one method of discriminating between pace pulses—including for biventricular pacing. At 800, the method is initiated in an "indeterminate" state with respect to any pace pulse locations. At 802, the method includes waiting for a detected pace pulse. At 804, a determination is made (e.g., using the characterizing information discussed above) of whether three different pace pulses have been detected. If not, then a determination is made at 806 (e.g., using the characterizing information discussed above) of whether two different pace pulses have been detected. If not, then characterizing information (e.g., amplitude, pulsewidth, etc.) is stored at 808, and the pace pulse is displayed with an "indeterminate" annotation. Then, at 810, it is noted whether a ventricular depolarization occurred within a predetermined time period (before or after) of the pace pulse, before returning to the indeterminate state 800.

At 804, if three different pace pulses were detected, then, at 812, it is determined whether the three distinct classes of pace pulses that are defined by these three different pace pulses have been assigned locations (e.g., atrial, ventricular, etc.). If not, then at 814, location assignments are computed, such as described above, using Table 3. If, at 814, the location assignment is invalid or indeterminate (as described in Table 3), then process flow returns to the indeterminate state at 800. If, at 814, valid locations can be assigned, such as by using Table 3, then process flow proceeds to 816. At 816, subsequently detected pace pulses are each matched to one of the distinct classes, for obtaining the location assignment for that particular class. At 818, such matched paces are annotated with the appropriate location information for display. If, at 816, subsequently detected paces do not match the distinct classes (e.g., the amplitude has changed, the pulsewidth has changed, etc.), then at 820, input "noise" is deemed to exist. In response, the distinct classes and location assignments are cleared, the anomalous pace is marked for display as "indeterminate," and process flow returns to the indeterminate state at 800.

At 804, if three different paces have not been detected (after detecting at least three paces), and at 806, two different paces have been detected, and at 812 the two different types of paces have not already been assigned location information, then, at 814, such location information is assigned using any technique appropriate for distinguishing the locations of two different types of pace pulses—for example, the technique described in Table 2, above.

The above examples have been discussed with respect to an external device that operates independently of the implanted device. For example, an external ECG monitor typically operates independently from the implanted device (e.g., without any communication with or information about the implanted device). However, the above systems, devices, and methods are also useful for an external device that does not operate independently of the implanted device. One such example is an external programmer that telemetrically communicates with an implanted device.

In an embodiment where the external device is capable of obtaining information about the implanted device, then the above systems, devices, and methods can be modified to incorporate the use of such information. In one example, the external device is aware that the right ventricular pacing pulse is programmed to a different amplitude than the left ventricular pacing pulse, and can recognize such different characterizing information as discussed above, then the display can appropriately annotate the ventricular pace pulses with more specific information (e.g., RV and LV rather than V1 and V2). In another example, if the external device is a programmer that communicates with the implanted device to change its pulsewidth, amplitude, and/or other characterizing features, then the present systems, devices, and methods may use that information, thereby reducing the need to declare input "noise" and improving the ability to detect and identify pace pulses with greater specificity.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. A system comprising:
   first, second, and third input terminals to receive heart signals from respective external first, second, and third electrodes attached to a subject;
   at least one pace pulse detector circuit, coupled to the first, second, and third input terminals, to detect from the heart signals first and second pace pulses delivered to differentelectro locations of the heart as electrostimulations for evoking responsive contractions at the different locations of the heart, the pace pulse detector circuit comprising an amplifier circuit to provide polarity information about the first and second pace pulses; and
   a logic circuit, coupled to the pace pulse detector circuit, configured to assign a first location assignment to the first and a second location assignment to the second pace pulse using at least in part the polarity information about the first and second pace pulses, wherein the first and second location assignments represent the different locations of the heart at which the first and second pace pulses were respectively delivered, and wherein the first and second location assignments discriminate at least between atrial and ventricular locations using the polarity information about the first and second pace pulses.

2. The system of claim 1, further comprising the external first, second, and third electrodes to couple to the first, second, and third input terminals, respectively.

3. The system of claim 2, in which the first second and third electrodes define a first vector between the first and second electrodes, a second vector between the first and third electrodes, and a third vector between the second and third electrodes, such that the first electrode is negative with respect to the second and third electrodes, and the second electrode is positive with respect to the first electrode and negative with respect to the third electrode, and the third electrode is positive with respect to the first and second electrodes.

4. The system of claim 3, in which the logic circuit is configured such that, if a polarity of the first pace pulse is detected as positive for both the second and third vectors, then the first pace pulse is assigned to an atrial location and the second pace pulse is assigned to a ventricular location.

5. The system of claim 3, in which the logic circuit is configured such that, if a polarity of the first pace pulse is detected as negative for both the second and third vectors, then the first pace pulse is assigned to a ventricular location and the second pace pulse is assigned to an atrial location.

6. The system of claim 3, in which the logic circuit is configured such that:
   if a polarity of the first pace pulse is detected as positive for both the second and third vectors, and the polarity of the second pace pulse is detected as negative for both the second and third vectors, then the first pace pulse is assigned to an atrial location and the second pace pulse is assigned to a ventricular location; and
   if a polarity of the first pace pulse is detected as negative for both the second and third vectors, and the polarity of the second pace pulse is detected as positive for both the second and third vectors, then the first pace pulse is assigned to a ventricular location and the second pace pulse is assigned to an atrial location.

7. The system of claim 3, further comprising a depolarization detector circuit, coupled to at least two of the first, second, and third inputs, to detect whether a ventricular depolarization occurred within a predetermined time period of at least one of the first and second pace pulses, and in which the logic circuit is configured such that, if at least one of the first and second pace pulses is detected as having a different polarity between the second and third vectors, a location classification is assigned to the at least one of the first and second pace pulses at least in part using information about whether the ventricular depolarization occurred within the predetermined time period.

8. A method comprising:
receiving heart signals from external first, second, and third electrodes attached to a subject;
detecting respective electric fields of at least one first pacing pulse delivered to a first location of the heart and at least one second pacing pulse delivered to a second location of the heart as electrostimulations for evoking responsive contractions at the different locations of the heart; and
assigning one of first and second location assignments to each of the first and second pacing pulses at least in part using respective polarities of the respective electric fields, wherein the first and second location assignments represent the different locations of the heart at which the first and second pace pulses were respectively delivered, and wherein the first and second location assignments discriminate at least between atrial and ventricular locations using the polarity information about the first and second pace pulses.

9. The method of claim 8, in which the first, second, and third electrodes define a first vector between the first and second electrodes, a second vector between the first and third electrodes, and a third vector between the second and third electrodes, such that the first electrode is negative with respect to the second and third electrodes, and the second electrode is positive with respect to the first electrode and negative with respect to the third electrode, and the third electrode is positive with respect to the first and second electrodes.

10. The method of claim 9, in further comprising:
attaching the first and second electrodes above the heart;
attaching the third electrode below the heart;
attaching the first electrode near a right arm of the subject; and
attaching the second electrode near a left arm of the subject.

11. The method of claim 9, in which the assigning includes, if the polarity of the first pace pulse is detected as positive for both the second and third vectors, then assigning the first pace pulse to an atrial location and assigning the second pace pulse to a ventricular location.

12. The method of claim 9, in which the assigning includes, if the polarity of the first pace pulse is detected as negative for both the second and third vectors, then assigning the first pace pulse to a ventricular location and assigning the second pace pulse to an atrial location.

13. The method of claim 9, in which the assigning includes, if at least one of the first and second pace pulses is detected as having a different polarity between the second and third vectors:
detecting whether a ventricular depolarization occurred within a predetermined time period of the at least one of the first and second pace pulses that was detected as having a different polarity between the second and third vectors; and
assigning a location classification to the at least one of the first and second pace pulses at least in part using information about whether the ventricular depolarization occurred within the predetermined time period.

14. The method of claim 8, further comprising displaying an indication of the location classification in correspondence with an indication of at least one of the first and second pace pulses.

15. A system comprising:
first, second, and third input terminals to receive heart signals from respective external first, second, and third electrodes attached to a subject;
at least one pace pulse detector circuit, coupled to the first, second, and third input terminals, to detect from the heart signals first and second pace pulses delivered to different locations of the heart as electrostimulations for evoking responsive contractions at the different locations of the heart, and to provide at least one of an amplitude of the pace pulses, a pulsewidth of the pace pulses, and a time difference between one of the pace pulses and a corresponding heart depolarization evoked by one of the pace pulses;
a depolarization detector circuit, coupled to at least one of the first, second, and third inputs, to detect whether a corresponding heart depolarization occurred within a predetermined time period of at least one of the first and second pace pulses; and
a logic circuit, coupled to the pace pulse detector circuit, and configured to classify the pace pulses into distinct classes using at least one of the amplitude, the pulsewidth, the polarity, and the time difference, and to compute location assignments for the distinct classes at least in part using the detected heart depolarizations associated with the pace pulses, wherein the location assignments represent the different locations of the heart at which the first and second pace pulses were respectively delivered, and wherein the location assignments discriminate at least between atrial and ventricular locations using the polarity information about the first and second pace pulses.

16. The system of claim 15, in which the logic circuit is configured to assign at least one of the distinct classes to a ventricular location if the at least one of the distinct classes includes at least one pace pulse that is accompanied by a ventricular depolarization within a predetermined time period of the at least one pace pulse.

17. The system of claim 15, further comprising the external first, second, and third electrodes to couple to the first, second, and third input terminals, respectively.

18. The system of claim 17, in which the first second and third electrodes define a first vector between the first and second electrodes, a second vector between the first and third electrodes, and a third vector between the second and third electrodes, such that the first electrode is negative with respect to the second and third electrodes, and the second electrode is positive with respect to the first electrode and negative with respect to the third electrode, and the third electrode is positive with respect to the first and second electrodes.

19. A method comprising:
receiving heart signals from external first, second, and third electrodes attached to a subject;
detecting pace pulses from the heart signals, wherein the pace pulses are delivered as electrostimulations for evoking responsive contractions at different locations of the heart;
detecting any heart depolarizations evoked by the pace pulses;
detecting at least one of an amplitude of the pace pulses, a pulsewidth of the pace pulses, a polarity of the pace pulses, and a time difference between each one of the pace pulses and a corresponding heart depolarization evoked by one of the pace pulses;

classifying the pace pulses into distinct classes using at least one of the amplitude, the pulsewidth, the polarity, and the time difference; and computing location assignments for the distinct classes at least in part using the detected heart depolarizations associated with the pace pulses, wherein the location assignments represent the different locations of the heart at which the pace pulses were respectively delivered, and wherein the location assignments discriminate at least between atrial and ventricular locations using the polarity information about the pace pulses.

20. The method of claim 19, in which the computing the location assignments for the distinct classes includes assigning at least one of the distinct classes to a ventricular location, if the at least one of the distinct classes includes at least one pace pulse that is accompanied by a ventricular depolarization within a predetermined time period of the at least one pace pulse.

21. The method of claim 19, further comprising displaying an indication of at least one of the location assignments in correspondence with a corresponding indication of the pace pulse.

* * * * *

UNITED STATES PATENT AND TRADEMARK OFFICE
CERTIFICATE OF CORRECTION

PATENT NO. : 7,336,998 B2
APPLICATION NO. : 10/608825
DATED : February 26, 2008
INVENTOR(S) : Yonce It is certified that error appears in the above-identified patent and that said Letters Patent is hereby corrected as shown below:

In column 7, line 16, after "214" insert -- , --.

In column 10, line 2, in Claim 1, delete "differentelectro" and insert -- different --, therefor.

In column 10, line 23, in Claim 3, delete "first second" and insert -- first, second, --, therefor.

In column 12, line 45, in Claim 18, delete "first second" and insert -- first, second, --, therefor.

Signed and Sealed this

Eighth Day of July, 2008

JON W. DUDAS
*Director of the United States Patent and Trademark Office*